US012668767B2

(12) United States Patent
Shinde et al.

(10) Patent No.: US 12,668,767 B2
(45) Date of Patent: Jun. 30, 2026

(54) MASSIVELY PARALLEL HIGH THROUGHPUT SINGLE-CELL OPTOPORATION

(71) Applicant: INDIAN INSTITUTE OF TECHNOLOGY MADRAS (IIT MADRAS), Chennai (IN)

(72) Inventors: Pallavi Shinde, Chennai (IN); Srabani Kar, Chennai (IN); Tuhin Subhra Santra, Chennai (IN)

(73) Assignee: INDIAN INSTITUTE OF TECHNOLOGY MADRAS (IIT MADRAS), Chennai (IN)

( * ) Notice: Subject to any disclaimer, the term of this patent is extended or adjusted under 35 U.S.C. 154(b) by 588 days.

(21) Appl. No.: 18/006,098

(22) PCT Filed: Jul. 21, 2021

(86) PCT No.: PCT/IN2021/050706
§ 371 (c)(1),
(2) Date: Jan. 19, 2023

(87) PCT Pub. No.: WO2022/018760
PCT Pub. Date: Jan. 27, 2022

(65) Prior Publication Data
US 2023/0279327 A1 Sep. 7, 2023

(30) Foreign Application Priority Data
Jul. 23, 2020 (IN) .............................. 202041031463

(51) Int. Cl.
*C12M 1/12* (2006.01)
*C12M 1/22* (2006.01)

(52) U.S. Cl.
CPC ............ *C12M 25/02* (2013.01); *C12M 23/10* (2013.01)

(58) Field of Classification Search
None
See application file for complete search history.

(56) References Cited

FOREIGN PATENT DOCUMENTS

WO 2012158631 A2 11/2012
WO 2019222872 A1 11/2019

OTHER PUBLICATIONS

Wu et al., Lab Chip, 18:3074-3078 (2018) (Year: 2018).*
Shinde et al., Proc. 15th Ann. IEEE Int., pp. 320-324 (2020) (Year: 2020).*
Shinde et al., Lab Chip, 23:4636-4651 (2023) (Year: 2023).*

(Continued)

*Primary Examiner* — Thomas J. Visone
(74) *Attorney, Agent, or Firm* — Renner, Otto, Boisselle & Sklar, LLP

(57) ABSTRACT

Massively parallel high throughput single-cell optoperation and their uses thereof are disclosed. The disclosed method teaches the use of parallel single-cell printing technique using SU-8 membrane and nanosecond pulsed laser to espouse on single-cell with micro-dish pattern structure. The platform is able to effectively deliver different (small to large) cargo in a different cell type with high transfection efficiency and high cell viability at parallel single-cell resolution. The proposed Bio-MEMS device has potential applications in personalized and regenerative medicine.

4 Claims, 4 Drawing Sheets

(56)         References Cited

OTHER PUBLICATIONS

Wu, et al. Massively parallel delivery of large cargo into mammalian cells with light pulses. Nat Method. 12:435-444. Apr. 6, 2015 Abstract, Introduction, Sections | The design and operating principle of BLAST and 'Mechanism of opening transient cell-membrane pores'.

Shinde, et al. Current Trends of Microfluidic Single-Cell Technologies, International Journal of Molecular Sciences, 19 (10) :3143. Oct. 12, 2018 Section 4.2.

Wu, et al. Microfluidic-Based Single-Cell Study: Current Status and Future Perspective, Molecules,23 (9) :2347. Sep. 13, 2018 Section bridging pp. 11 & 12.

International Search Report and Written Opinion for corresponding Application No. PCT/IN2021/050706, issued on Nov. 22, 2021.

* cited by examiner

200

MASSIVELY PARALLEL HIGH THROUGHPUT SINGLE-CELL OPTOPORATION

This application is a national phase of International Application No. PCT/IN2021/050706 filed Jul. 21, 2021, which claims priority to Indian Application No. 202041031463 filed Jul. 23, 2020, each of which is hereby incorporated herein by reference in its entirety.

TECHNICAL FIELD

The present invention generally relates to massively parallel high throughput single cell printing technology. The present invention is additionally related to photoporation and intracellular delivery techniques. The present invention also relates to methods for printing cells in massively high throughput fashion at single cell resolution. The present inventions specifically relates to massively parallel high throughput single-cell optoporation and their uses thereof.

BACKGROUND OF THE INVENTION

Single cell intracellular delivery is a fast emerging field of interest in cellular biology and therapeutic applications. Single cell intracellular delivery is associated with several challenges due to impermeability of cargo to the cell membrane barrier. Typically, in such conventional intracellular delivery applications, the cell membrane is locally disrupted for allowing cargo passage into the cytosol in order to thereby create its therapeutic effect.

In recent years, transfection technique is widely adapted for introducing foreign cargo into the single-cells. Majority of the prior art techniques are cell specific bulk cargo delivery applications with low efficiency and cell viability. The prior art intracellular delivery approaches are performed in bulk which provides an average ensemble data, losing rare low frequency information. Besides, reliable results require huge data from multiple cells.

Hence, to ensure huge data on each individual cells it highly important to carry out delivery experiments on a large number of single cells simultaneously i.e., in parallel high throughput manner. Adapting parallel high throughput approach ensures the same experimental conditions conserving heterogeneity in the cell population. Furthermore, the collection of data from individual cells provides information about rare low frequency alleles in the cell population.

However, cell culture is a random event with cells getting attached at any location on the substrate. Further, the cells can clutter up at some locations and cannot be monitored individually. The cells divide over time and the heredity of the cell is lost in the cluster of cells. The cells behave differently from their in vivo microenvironment. Also, the cells lack organization to form tissue in vitro, due to lack of proper cell communication.

The cell arrangement is random and does not exhibit tissue alike arrangement. It is therefore highly desirable for a technique to organize single cell in desired pattern such that various biophysical aspects as well as cell signaling can be studied. Also, the cells could be delivered with desired molecules such that their behavior as individual in the group can be studied.

Based on the foregoing a need therefore exists for an improved massively parallel delivery approach that ensures uniform experimental conditions with uniform cargo delivery to a large number of individual cells. Also, a need exists for a method for printing massively parallel high throughput single cell and their uses thereof, as discussed in greater detail herein.

SUMMARY OF THE INVENTION

The following summary is provided to facilitate an understanding of some of the innovative features unique to the disclosed embodiment and is not intended to be a full description. A full appreciation of the various aspects of the embodiments disclosed herein can be gained by taking the entire specification, claims, drawings, and abstract as a whole.

Therefore, one aspect of the disclosed embodiment is to provide for an improved massively parallel high throughput single cell printing technology.

It is another aspect of the disclosed embodiment to provide for improved for printing cells in massively high throughput fashion at single cell resolution.

It is further aspect of the disclosed embodiment to provide for an improved method for printing massively parallel high throughput single cell and their uses thereof.

The aforementioned aspects and other objectives and advantages can now be achieved as described herein.

Massively parallel high throughput single-cell optoporation and their uses thereof.

The method teaches use of parallel single-cell printing technique using SU-8 membrane and nano-second pulsed laser to espouse on single-cell with micro-dish pattern structure. The platform is able to effectively deliver different (small to large) cargo in a different cell type with high transfection efficiency and high cell viability at parallel single-cell resolution. The bio-MEMS device proposed herein has potential application in personalized medicine and regenerative medicine applications.

A thin membrane material (SU-8 membrane material) with an array of holes is fabricated using photolithography technique in order to use the membrane material as a cell printing platform, where the cells are cultured and seeded in a high density, wherein the size of the array of holes of the membrane material are designed such that the single-cells can pass through the holes of the membrane material. An array of micro dish patterned metal on a glass substrate was flipped and placed on the membrane material, such that the metal faces the patterned cells. The cell printing platform is exposed with a pulsed laser at near infrared wavelength (NIR) to create plasmonic/vapor induced bubbles wherein the bubbles create pores in the cell membrane, due to shock waves generated by bubble expansion, coalesce and collapse. The membrane can be used to diffuse desired molecules in the single-cell in massively parallel high throughput fashion.

The cell printing platform is prepared by cutting a micro slide glass was cut into a square (2×2 cm) and cleaning the glass with standard piranha cleaning process. The glass was further dried with nitrogen blow and dehydrated. SU-8 3005 was spin coated on the substrate, patterned and then ultrasonicated in developer for 1 minute to release the patterned membrane. The sample was cleaned with iso propanol alcohol (IPA) and deionized water, dried using nitrogen.

The membrane was then peeled off from the substrate and put into a petri dish. The petri dish was UV treated with the Su8 membrane for 2 hrs. Cells were cultured and seeded in a high density on the Su8 membrane. The size of the SU-8 membrane holes are designed such that single-cells can pass through the holes. In one embodiment of the proposed invention, the Su8 membrane with 35 μm through holes was found suitable for SiHa cells. However, the diameter of through holes in the Su8 membrane for achieving single cell patterning can vary from cell to cell. Please note that by tuning the diameter of through holes, the number of cells per patterned region can be controlled.

Additionally, heterogeneous cell lines can also be co-cultured and patterned using the Su8 membrane which can have potential applications in studying cell signaling, cell heterogeneity, intracellular delivery and cell therapy and diagnostics etc.

Further, an array of micro dish patterned metal on glass substrate was flipped and placed on the Su8 membrane, such that the metal faces the patterned cells. The sample was exposed with pulsed laser at near infrared wavelength (NIR) to create plasmonic or vapor induced bubbles. These bubbles create pore in the cell membrane due to shock waves generated by bubble expansion, coalesce and collapse. Once, membrane pore is created, it can be used to diffuse any desired molecules in the single-cell in massively parallel high throughput fashion. The invention proposed herein thereby teaches a novel and inventive approach for intro-duction of foreign cargo into single-cells with high effi-ciency and high cell viability is a wide range of cellular biological research and therapeutic applications.

BRIEF DESCRIPTION OF DRAWINGS

The drawings shown here are for illustration purpose and the actual system will not be limited by the size, shape, and arrangement of components or number of components rep-resented in the drawings.

DETAILED DESCRIPTION

The particular values and configurations discussed in these non-limiting examples can be varied and are cited merely to illustrate at least one embodiment and are not intended to limit the scope thereof.

FIG. 1(a)-1(i) illustrates a schematic view 100 of the cell culturing platform (SU-8 membrane) demonstrating various steps involved in method of printing massively parallel high throughput single cell, in accordance with the disclosed embodiments. The method teaches use of parallel single-cell printing technique using SU-8 membrane and nano-second pulsed laser to espouse on single-cell with micro-dish pat-tern structure. The platform is able to effectively deliver different (small to large) cargo in a different cell type with high transfection efficiency and high cell viability at parallel single-cell resolution. The bio-MEMS device proposed herein has potential application in personalized medicine and regenerative medicine applications.

Figure 1:
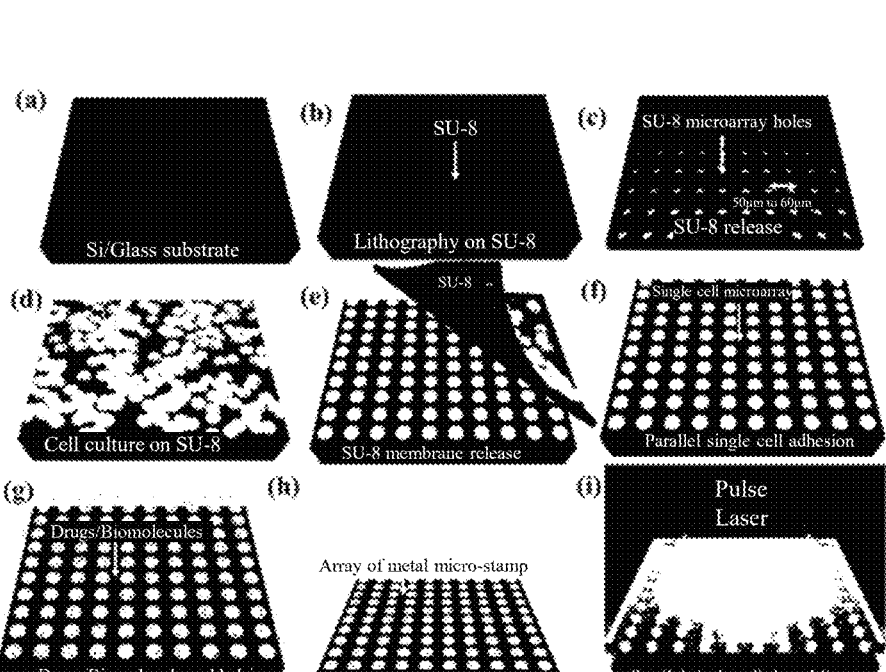
FIG. 1(a)-1(i) illustrates a schematic view 100 of the cell culturing platform (SU-8 membrane) demonstrating various steps involved in method of printing massively parallel high throughput single cell, in accordance with the disclosed embodiments.

A thin membrane material (SU-8 membrane material) with an array of holes is fabricated using photolithography technique in order to use the membrane material as a cell printing platform, where the cells are cultured and seeded in a high density (as shown in FIG. 1(d)), wherein the size of the array of holes of the membrane material are designed such that the single-cells can pass through the holes of the membrane material, as shown in FIG. 1(a) and FIG. 1(b). An array of micro dish patterned metal on a glass substrate was flipped and placed on the membrane material, such that the metal faces the patterned cells, as illustrated in FIG. 1(h). The cell printing platform is exposed with a pulsed laser at near infrared wavelength (NIR) to create plasmonic/vapor induced bubbles wherein the bubbles create pores in the cell membrane, due to shock waves generated by bubble expan-sion, coalesce and collapse. The membrane can be used to diffuse desired molecules in the single-cell in massively parallel high throughput fashion, as illustrated in FIG. 1(i).

Figure 2:
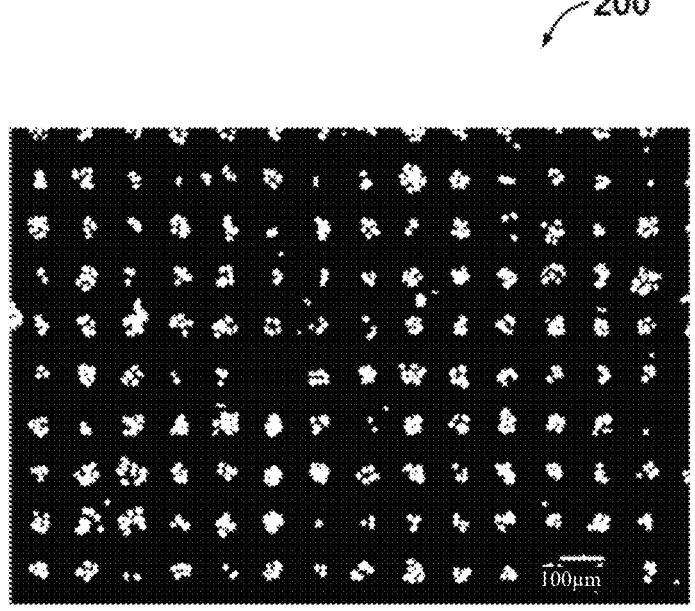
FIG. 2 illustrate a exemplary graphical representation 200 of single-cells printing (calcein AM staining) using SU-8 membrane holes using an array of 50 μm hole size and 100 μm interspacing, in accordance with the disclosed embodi-ments.

FIG. 2 illustrate a exemplary graphical representation 200 of single-cells printing (calcein AM staining) using SU-8 membrane holes using an array of 50 μm hole size and 100 μm interspacing, in accordance with the disclosed embodi-ments. FIG. 2 shows successfully colonies of single-cell printing using SU-8 membrane with 50 μm hole size and 100 μm interspacing (Calcein AM staining indicating live cells with an array of single-cells).

Figure 3:
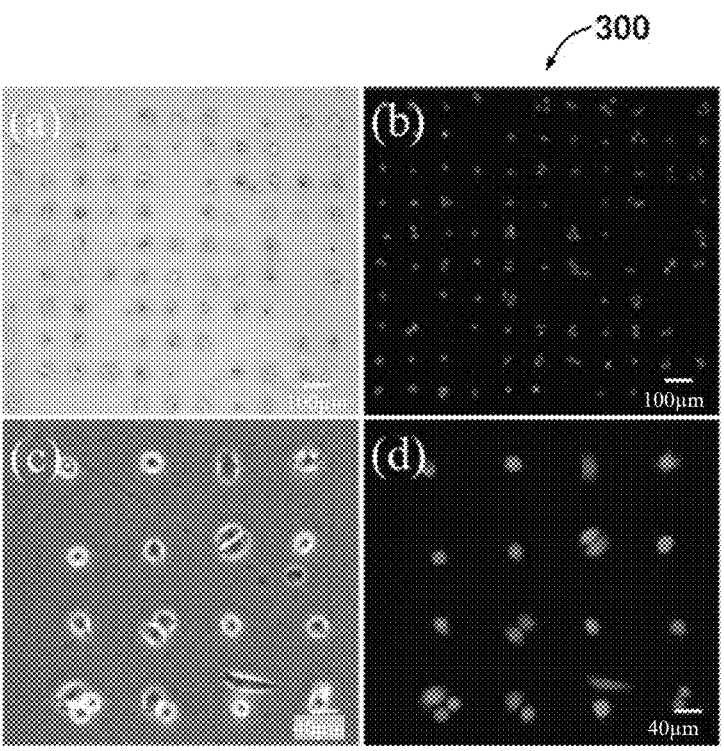
FIG. 3 illustrates an exemplary graphical representation 300 of single-cell (SiHa cells) printing using SU-8 mem-brane holes using an array of 40 μm holes size and 100 μm interspacing, in accordance with the disclosed embodiments.

FIG. 3 illustrates an exemplary graphical representation 300 of single-cell (SiHa cells) printing using SU-8 mem-brane holes using an array of 40 μm holes size and 100 μm interspacing, in accordance with the disclosed embodiments. FIGS. 3a and 3b illustrates the optical micrograph images of single cell and FIGS. 3c and 3d illustrates the cell permeable Calcein AM images after an array of single-cell adhesion.

The cell printing platform is prepared by cutting a micro slide glass was cut into a square (2×2 cm) and cleaning the glass with standard piranha cleaning process. The glass was further dried with nitrogen blow and dehydrated. SU-8 3005 was ultra-sonicated for 1 minute to release the membrane and the sample was cleaned with iso propanol alcohol (IPA) and deionized water, dried using nitrogen, as shown in FIG. 1(c).

The membrane was then peeled off from the substrate and put into a petri dish, as illustrated in FIG. 1(e). The petri dish was UV treated with the Su8 membrane for 2 hrs. Cells were cultured and seeded in a high density on the Su8 membrane. The size of the SU-8 membrane holes are designed such that single-cells can pass through the holes. In one embodiment of the proposed invention, the Su8 membrane with 35 μm through holes was found suitable for SiHa cells. However, the diameter of through holes in the Su8 membrane for achieving single cell patterning can vary from cell to cell. Please note that by tuning the diameter of through holes, the number of cells per patterned region can be controlled.

Additionally, heterogeneous cell lines can also be co-cultured and patterned using the Su8 membrane which can have potential applications in studying cell signaling, cell heterogeneity, intracellular delivery and cell therapy and diagnostics etc, as illustrated in FIG. 1(e).

Further, an array of micro dish patterned metal on glass substrate was flipped and placed on the Su8 membrane, such that the metal faces the patterned cells. The sample was exposed with pulsed laser at near infrared wavelength (NIR) to create plasmonic or vapor induced bubbles. These bubbles create pore in the cell membrane due to shock waves generated by bubble expansion, coalesce and collapse. Once, membrane pore is created, it can be used to diffuse any desired molecules in the single-cell in massively parallel high throughput fashion.

Figure 4:
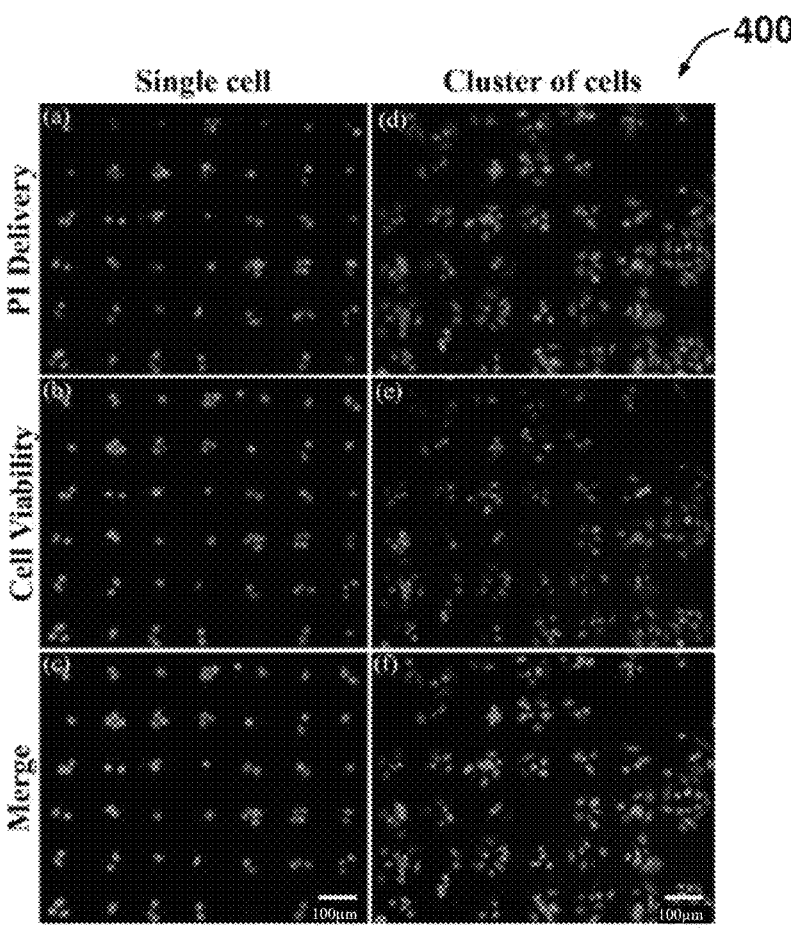
FIG. 4 illustrates a graphical representation 400 of fluo-rescence image of massively parallel high throughput single-cell drug delivery to spatially isolated SiHa cells (Cervical cancer), in accordance with the disclosed embodiments.

FIG. 4 illustrates a graphical representation 400 of fluorescence image of massively parallel high throughput single-cell drug delivery to spatially isolated SiHa cells (Cervical cancer), in accordance with the disclosed embodiments. FIGS. 4*a* and 4*d* illustrates successful PI dye delivery into single-cell. FIGS. 4*b* and 4*e* indicate cell permeable Calcein AM staining and cells are live after delivery. FIGS. 4*c* and 4*d* illustrates the merge image of FIG. 4*a*, 4*b*, 4*c* and 4*d* accordingly. The invention proposed herein thereby teaches a novel and inventive approach for introduction of foreign cargo into single-cells with high efficiency and high cell viability is a wide range of cellular biological research and therapeutic applications.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

We claim:

1. A method for printing a plurality of individual cells in parallel, said method comprising:

fabricating an SU-8 membrane material with an array of holes using a photolithography technique on a glass substrate in order to use the SU-8 membrane material as part of a cell printing platform, wherein the plurality of individual cells are cultured and seeded on the SU-8 membrane material, wherein a size of each hole in the array of holes of the SU-8 membrane material is designed such that respective individual cells of the plurality of individual cells can pass through each hole of the SU-8 membrane material to create a pattern of cells on the glass substrate;

flipping an array of microdish patterned metal on the glass substrate and placing the array of microdish patterned metal on the glass substrate, such that the array of microdish patterned metal faces the pattern of cells; and exposing the glass substrate with a pulsed laser at a near infrared wavelength (NIR) to create photothermal vapor induced bubbles, wherein the photothermal vapor induced bubbles create pores in a cell membrane of each of the individual cells of the plurality of individual cells and each cell membrane is used to diffuse desired molecules in each of the individual cells of the plurality of individual cells.

2. The method of claim 1, further comprising preparing the glass substrate by: cutting a glass microslide into a square, cleaning the glass microslide with a standard piranha cleaning process, drying the glass microslide with nitrogen blow, and dehydrating the glass microslide.

3. The method of claim 2, wherein fabricating the SU-8 membrane material comprises spin coating SU-8 3005 on the glass substrate, patterning the SU-8 3005, ultra-sonicating the SU-8 3005 in a developer for 1 minute to release the SU-8 membrane material from the glass substrate, cleaning the SU-8 membrane material with isopropyl alcohol (IPA) and deionized water, and drying the SU-8 membrane material using nitrogen.

4. The method of claim 2, further comprising peeling the SU-8 membrane material off from the glass substrate and putting the SU-8 membrane material into a petri dish wherein the petri dish was UV treated with the Su8 membrane for 2 hrs.

* * * * *